US010912875B2

(12) United States Patent
Beiriger (10) Patent No.: US 10,912,875 B2
(45) Date of Patent: Feb. 9, 2021

(54) SENSING NEGATIVE PRESSURE WITH A PRESSURE TRANSDUCER (71) Applicant: Fresenius Medical Care Holdings, Inc., Waltham, MA (US)

(72) Inventor: Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 505 days.

(21) Appl. No.: 14/510,199

(22) Filed: Oct. 9, 2014

(65) Prior Publication Data
US 2016/0101226 A1 Apr. 14, 2016

(51) Int. Cl.
*A61M 1/26* (2006.01)
*A61M 1/28* (2006.01)
*A61M 1/36* (2006.01)
*F04B 43/00* (2006.01)
*F04B 43/04* (2006.01)
*F04B 49/08* (2006.01)

(52) U.S. Cl.
CPC .............. *A61M 1/267* (2014.02); *A61M 1/28* (2013.01); *A61M 1/3639* (2013.01); *A61M 1/3641* (2014.02); *F04B 43/0081* (2013.01); *F04B 43/04* (2013.01); *F04B 49/08* (2013.01); *A61M 2205/12* (2013.01); *A61M 2205/3331* (2013.01)

(58) Field of Classification Search
CPC ...... A61M 1/267; A61M 1/28; A61M 1/3639; A61M 2205/3331; A61M 2205/14; F04B 49/08
See application file for complete search history.

(56) References Cited

U.S. PATENT DOCUMENTS 4,923,444 A * 5/1990 Daoud ............... A61M 5/16854
600/561
5,307,684 A * 5/1994 Moss ..................... G01L 9/0051
73/706
(Continued)

FOREIGN PATENT DOCUMENTS

CN 1165484 11/1997
CN 101446280 6/2009
(Continued)

OTHER PUBLICATIONS

5008 Hemodialysis System Operating Instructions, software version 3.52, Edition 5/09.06, Part No. M38 816 1, 328 pages, Sep. 2006.
(Continued)

*Primary Examiner* — Jenna Zhang
(74) *Attorney, Agent, or Firm* — Fish & Richardson P.C.

(57) ABSTRACT

A medical system includes a medical fluid pumping machine comprising a pressure sensor, a medical fluid line set comprising a fluid line in fluid communication with a fluid passage formed between a diaphragm and a base, the medical fluid line set being configured to be connected to the medical fluid pumping machine in a manner such that the diaphragm of the medical fluid line set aligns with the pressure sensor of the medical fluid pumping machine, and a member configured to apply a positive force to the pressure sensor when the medical fluid line set is connected to the medical fluid pumping machine and the fluid passage is at atmospheric pressure.

27 Claims, 8 Drawing Sheets

(56) References Cited

U.S. PATENT DOCUMENTS

| | | | |
|---|---|---|---|
| 5,563,347 A * | 10/1996 | Martin | G01L 19/14 |
| | | | 73/706 |
| 5,614,677 A * | 3/1997 | Wamsiedler | G01L 19/144 |
| | | | 700/186 |
| 5,644,285 A * | 7/1997 | Maurer | G01L 9/0052 |
| | | | 338/39 |
| 6,280,406 B1 * | 8/2001 | Dolecek | A61M 1/3624 |
| | | | 210/645 |
| 6,484,383 B1 | 11/2002 | Herklotz | |
| 6,536,278 B1 | 3/2003 | Scagliarini | |
| 6,542,761 B1 * | 4/2003 | Jahn | A61M 1/3639 |
| | | | 600/310 |
| 6,725,726 B1 | 4/2004 | Adolfs et al. | |
| 7,021,148 B2 | 4/2006 | Kuhn et al. | |
| 7,069,788 B2 | 7/2006 | Teugels | |
| 7,152,479 B2 * | 12/2006 | Krause | G01L 9/0027 |
| | | | 73/715 |
| 7,603,907 B2 | 10/2009 | Reiter et al. | |
| 7,935,074 B2 | 5/2011 | Plahey et al. | |
| 8,110,104 B2 | 2/2012 | Crnkovich et al. | |
| 8,343,346 B2 | 1/2013 | Crnkovich et al. | |
| 8,617,070 B2 * | 12/2013 | Imran | A61B 5/0538 |
| | | | 600/309 |
| 8,663,463 B2 | 3/2014 | Frazer et al. | |
| 8,685,244 B2 | 4/2014 | Heyes et al. | |
| 8,960,010 B1 | 2/2015 | Crnkovich et al. | |
| 2002/0104786 A1 | 8/2002 | Chevallet | |
| 2002/0107468 A1 * | 8/2002 | Chevallet | G01L 19/0023 |
| | | | 604/5.01 |
| 2003/0199803 A1 * | 10/2003 | Robinson | A61M 1/0218 |
| | | | 604/6.04 |
| 2004/0019313 A1 * | 1/2004 | Childers | A61M 1/28 |
| | | | 604/5.01 |
| 2005/0063831 A1 * | 3/2005 | Fathallah | A61M 5/14224 |
| | | | 417/63 |
| 2007/0179433 A1 * | 8/2007 | Jonsson | A61M 1/3639 |
| | | | 604/31 |
| 2007/0219480 A1 * | 9/2007 | Kamen | G05D 7/0647 |
| | | | 604/20 |
| 2008/0243054 A1 * | 10/2008 | Mollstam | A61B 1/015 |
| | | | 604/31 |
| 2010/0114063 A1 * | 5/2010 | Recinella | A61M 25/0097 |
| | | | 604/508 |
| 2011/0015610 A1 | 1/2011 | Plahey et al. | |
| 2012/0181331 A1 * | 7/2012 | Beden | A61B 90/98 |
| | | | 235/375 |
| 2013/0018301 A1 * | 1/2013 | Weaver | A61M 1/3641 |
| | | | 604/28 |
| 2014/0114282 A1 * | 4/2014 | Gray | G05D 7/0647 |
| | | | 604/506 |
| 2014/0276421 A1 * | 9/2014 | Plahey | A61M 1/16 |
| | | | 604/151 |
| 2015/0314058 A1 * | 11/2015 | O'Mahony | F04B 49/002 |
| | | | 417/63 |
| 2015/0335809 A1 * | 11/2015 | Stuva | A61M 1/367 |
| | | | 137/15.01 |
| 2016/0089484 A1 * | 3/2016 | Lindley | G01L 19/0023 |
| | | | 73/715 |

FOREIGN PATENT DOCUMENTS

| | | |
|---|---|---|
| EP | 0947814 A2 | 10/1999 |
| JP | H1-109960 | 7/1989 |
| JP | H03-015732 | 1/1991 |
| JP | H03-049851 | 5/1991 |
| JP | 2002-233570 | 8/2002 |
| JP | 2004-531321 | 10/2004 |
| JP | 2013-516293 | 5/2013 |
| WO | WO 97/09074 | 3/1997 |
| WO | WO 03/000026 | 1/2003 |
| WO | WO 2004/081508 | 9/2004 |
| WO | WO 2011/085214 | 7/2011 |
| WO | WO2011119348 A2 | 9/2011 |
| WO | WO 2014/099779 | 6/2014 |

OTHER PUBLICATIONS

MultiFiltrate Operating Instructions, software version 5.2, Edition 12/11.12, Part No. M28 330 1, 274 pages, Nov. 2012.

Notification of Transmittal of the International Search Report and the Written Opinion of the International Searching Authority for corresponding PCT Application No. PCT/US2015/053929, dated Dec. 16, 2015, 12 pages.

International Preliminary Report on Patentability in International Application No. PCT/US2015/053929, dated Apr. 11, 2017, 7 pages.

* cited by examiner

SENSING NEGATIVE PRESSURE WITH A PRESSURE TRANSDUCER

TECHNICAL FIELD

This invention relates to sensing negative pressure with a pressure transducer.

BACKGROUND

Hemodialysis is a treatment used to support a patient with insufficient renal function. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During isolated ultrafiltration ("UF") on patients experiencing fluid overload, such as patients suffering from heart failure or acute or chronic renal failure, the patient's blood is passed through a hemofilter having a semi-permeable membrane that separate the filter into compartments. A pressure gradient within these compartments drives fluid across the semi-permeable membrane, allowing a predetermined percentage of plasma fluid in the blood to be removed by transport. The remaining blood is returned to the patient. Unlike HD, no dialysis solution or dialysate is passed through the dialyzer during UF.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

HD, UF, and PD apparatuses are typically configured to measure and control the pressure of fluids being removed from and/or returned to the patient. Such pressure measurements can be used for monitoring and controlling the apparatuses.

SUMMARY

In one aspect of the invention, a medical system comprises a medical fluid pumping machine comprising a pressure sensor, a medical fluid line set comprising a fluid line in fluid communication with a fluid passage formed between a diaphragm and a base, the medical fluid line set being configured to be connected to the medical fluid pumping machine in a manner such that the diaphragm of the medical fluid line set aligns with the pressure sensor of the medical fluid pumping machine, and a member configured to apply a positive force to the pressure sensor when the medical fluid line set is connected to the medical fluid pumping machine and the fluid passage is at atmospheric pressure.

Implementations can include one or more of the following features. The diaphragm and the base are parts of a pressure capsule to which the fluid line is connected. The diaphragm and the base are parts of a medical fluid cassette to which the fluid line is connected. The member enables the pressure sensor to detect positive and negative pressures generated within the fluid passage. The member is affixed to the diaphragm. The member is affixed to the pressure sensor and protrudes outwardly from a face of the medical fluid pumping machine. The member comprises a fluid pillow. The fluid pillow is an air pillow. The fluid pillow is configured to press the diaphragm against the pressure sensor to apply the positive force to the pressure sensor when the medical fluid line set is connected to the medical fluid pumping machine. The member is a spring. The spring is disposed in the fluid passage. The spring is configured to apply an outward force to the diaphragm to bias a portion of the diaphragm overlying the fluid passage away from the base. The spring is attached an outer surface of the diaphragm and protrudes away from the diaphragm.

In some implementations, the member is a disc that is attached to the diaphragm and protrudes outwardly from the diaphragm relative to the base. The member is a disc that is attached to the pressure sensor and protrudes outwardly from a face of the medical fluid pumping machine. The pressure sensor is configured to contact an outer surface of the diaphragm when the medical fluid line set is connected to the medical fluid pumping machine. The pressure sensor is configured to be calibrated to a zero reading while the positive force is applied to the pressure sensor.

In some implementations, the medical system further comprises a control unit that is in communication with pressure sensor and is configured to determine a medical fluid pressure based on a pressure detected by the pressure sensor. The control unit comprises a look-up table that provides a corrected fluid pressure for each pressure detected by the pressure sensor. The control unit is configured to calculate a corrected medical fluid pressure by inputting a pressure detected by the pressure sensor into an equation. The pressure sensor comprises a pressure transducer. The medical fluid pumping machine is a dialysis machine. The medical fluid pumping machine is a blood pumping machine and the pressure sensor is configured to detect a pressure of blood within the fluid passage.

In some implementations, a medical fluid line set comprises a fluid line in fluid communication with a fluid passage formed between a diaphragm and a base, the medical fluid line set being configured to be connected to a medical fluid pumping machine in a manner such that the diaphragm of the medical fluid line set aligns with a pressure sensor of the medical fluid pumping machine, and a member configured to apply a positive force to the pressure sensor when the medical fluid line set is connected to the medical fluid pumping machine and the fluid passage is at atmospheric pressure. The diaphragm, the base, and the member are parts of a pressure capsule to which the fluid line is connected. The diaphragm, the base, and the member are parts of a medical fluid cassette to which the fluid line is connected. The member comprises a fluid pillow. The member is a disc. The member is a spring.

In some implementations, medical fluid pumping machine comprises a pressure sensor, and a member that is affixed to the pressure sensor and protrudes outwardly from a face of the dialysis machine to contact a portion of a medical fluid line set when the medical fluid line set is connected to the medical fluid pumping machine. The pressure sensor is configured to be calibrated to a zero reading while a positive force is applied to the pressure sensor by the medical fluid line set. A control unit that is in communication with pressure sensor and is configured to determine a medical fluid pressure based on a pressure detected by the pressure sensor. The pressure sensor comprises a pressure transducer.

In some implementations, a method comprises applying an initial positive force to a pressure sensor of a medical fluid pumping machine by connected a medical fluid line set to the medical fluid pumping machine, applying an additional force to the pressure sensor, and detecting a combination of the initial positive force and the additional force. The additional force is a negative force. The method comprises calibrating the pressure sensor to a zero reading while the initial positive force is applied to the pressure sensor.

Implementations can include one or more of the following advantages.

The pressure sensor assemblies described herein can more reliably measure negative fluid pressures than certain known pressure sensors that use an air-tight seal and/or vacuum pressure to adhere a diaphragm of a pressure sensing capsule to a pressure transducer. In known sensors that rely on an air-tight seal to adhere the diaphragm to the pressure transducer, for example, any debris accumulating in the area between the diaphragm and the transducer can cause portions of the diaphragm to become decoupled from the pressure transducer, resulting in inaccurate pressure readings, particularly negative pressure readings. In sensors that rely on an active vacuum source to couple the diaphragm to the pressure transducer, a loss of vacuum results in decoupling of the diaphragm from the pressure transducer when negative fluid pressures are generated within an enclosure defined by the diaphragm. As a result of this decoupling, the negative fluid pressures cannot be accurately read by the pressure transducer. The sensors described herein do not rely on an air-tight seal or active vacuum pressure to couple the diaphragm to the pressure transducer. Many of the pressure sensor assemblies described herein include displacement devices or offset devices that permit negative pressure readings to be accurately obtained even if some debris is between the diaphragm and the pressure transducer and without the use of an active vacuum source.

A further advantage of the pressure sensor assemblies described herein is that it is not necessary to regularly check if the diaphragm is coupled to the pressure transducer. In certain fluid pumping systems that include pressure sensor assemblies that use an air-tight seal and/or active vacuum to couple a diaphragm to a pressure transducer, negative pressure is purposely generated within the fluid passage of the pressure sensor assembly on a regular basis to ensure those negative pressures can be detected by the pressure transducer. This testing requires regular interruptions of treatments (e.g., dialysis treatments) being carried out using such fluid pumping systems and thus decreases the efficiency of those treatments. The pressure sensor assemblies described herein obviate this loss of treatment efficiency.

Many of the pressure sensor assemblies described herein, as noted above, do not include active vacuum sources for coupling the diaphragm to the pressure transducer. Thus, these pressure sensor assemblies tend to be less expensive than known pressure sensor assemblies that use such active vacuum sources.

Other aspects, features, and advantages will be apparent from the description and drawings, and from the claims.

DETAILED DESCRIPTION

Certain aspects of this disclosure relate to medical fluid pumping systems (e.g., dialysis systems) that include a medical fluid pumping machine (e.g., a dialysis machine) having a pressure sensor and a medical fluid line set (e.g., a blood line set) having a pressure sensing portion that aligns with the pressure sensor when the medical fluid line set is secured to the medical fluid pumping machine. The pressure sensor and the pressure sensing portion of the medical fluid line set are configured to enable negative fluid pressures within the pressure sensing portion of the medical fluid line set to be detected by the pressure sensor. The pressure sensing portion of the medical fluid line set and/or the pressure sensor of the medical fluid pumping machine can, for example, include a displacement device or offset device that, when the medical fluid line set is secured to the medical fluid pumping machine, applies a positive gauge pressure to the pressure sensor even before a positive fluid pressure is generated within the sensing portion of the medical fluid line set. As a result of this initial positive pressure being applied to the pressure sensor, negative pressures generated within the pressure sensing portion of the medical fluid line set that have absolute values less than or equal to the initial positive pressure can be detected by the pressure sensor. The displacement devices or offset devices used to apply the initial positive pressure to the pressure sensor can be less complex than certain devices, such as active vacuum devices, that have been used to enable negative pressures to be detected within known medical fluid line sets.

Figure 1:
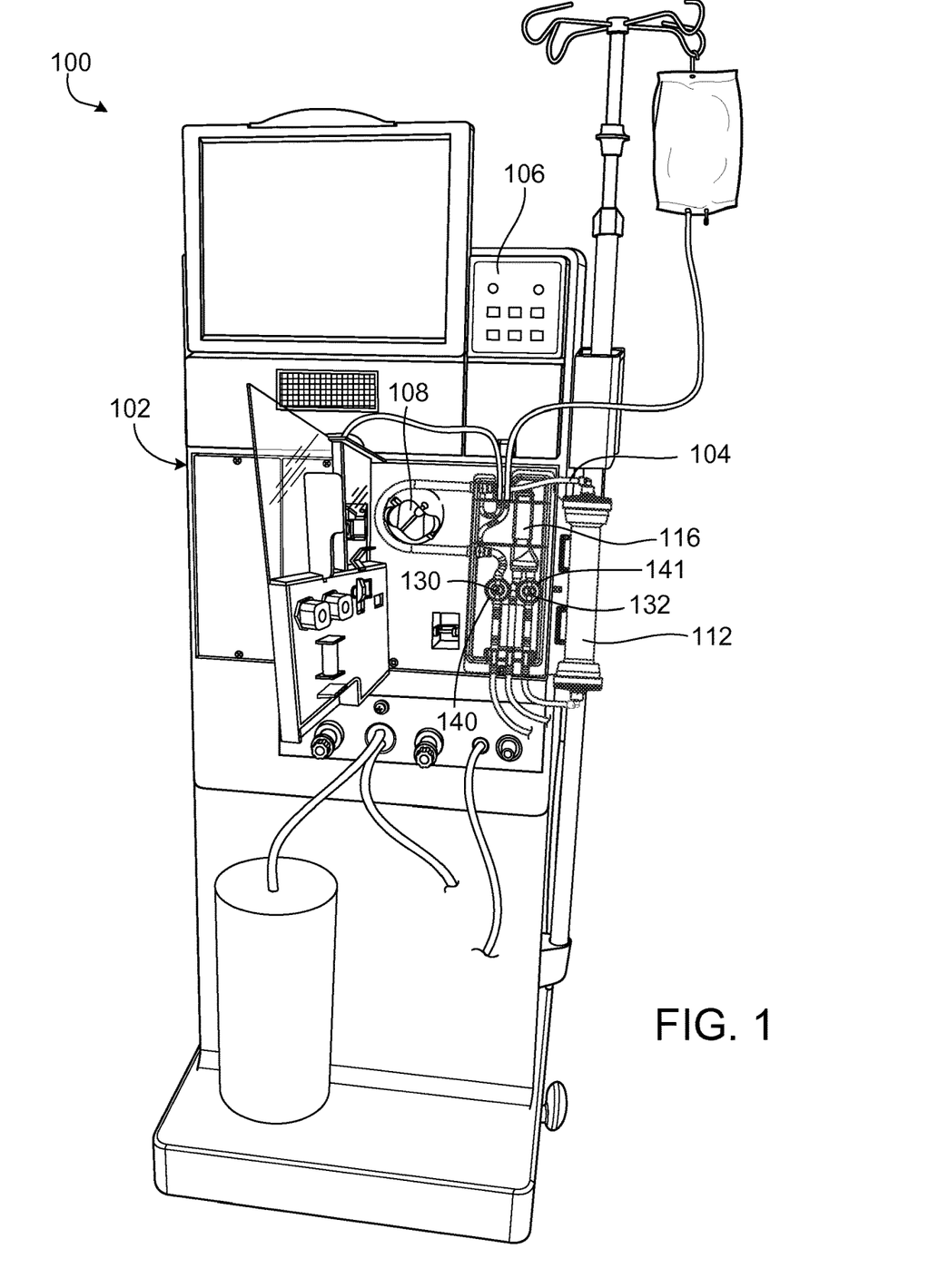
FIG. 1 is a schematic of a hemodialysis system including a disposable blood line set secured to a hemodialysis machine.

Referring to FIG. 1, a dialysis system 100 includes a dialysis machine 102 and a disposable blood line set 104 secured to the dialysis machine 102. The dialysis machine 102 includes a dialysis machine control unit (e.g., a microprocessor) 106, a blood pump 108, and a dialysate fluid circuit with one or more dialysate pumps to pump dialysate through the dialysis fluid circuit. During dialysis treatment, the blood pump 108 pumps blood through a first chamber of a dialyzer 112 connected to the blood line set 104. At the same time, dialysate is pumped through a second chamber of the dialyzer 112 to remove impurities from the blood by pulling those impurities across a membrane (e.g., microtubes) from the first chamber to the second chamber. In FIG. 1, an access door is shown in an open position to better show the components of the dialysis system 100, however the access door is in a closed position while the dialysis system 100 is in use.

Figure 2:
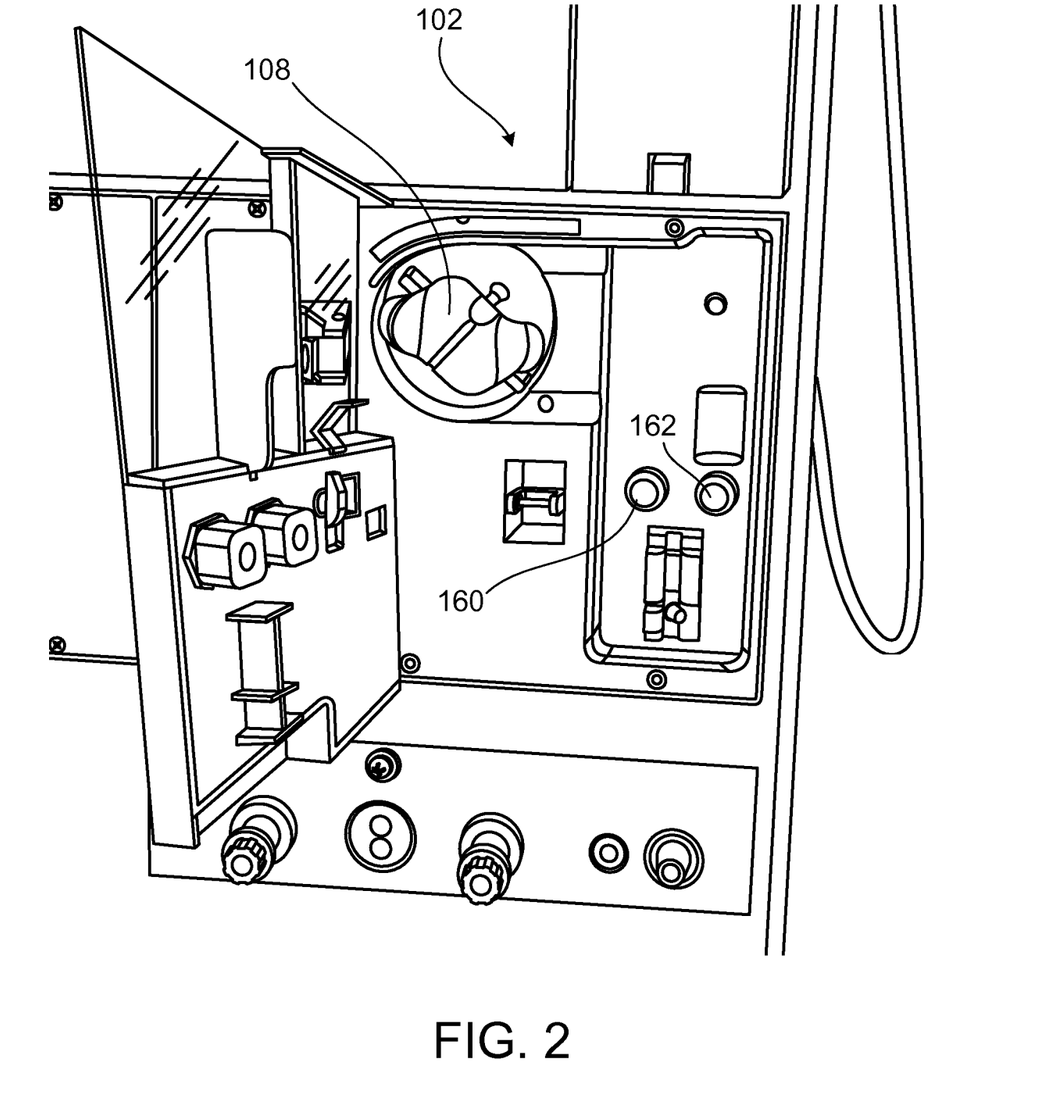
FIG. 2 is a schematic of a front face of the hemodialysis machine of FIG. 1.

As shown in FIG. 2, the dialysis machine 102 includes pressure transducers 160, 162 that are flush mounted on the face of the dialysis machine 102. The pressure transducers 160, 162 are arranged to align with and contact pressure capsules 130, 132 of the blood line set 104 when the blood line set 104 is secured to the dialysis machine 102. The pressure transducers 160, 162 are capable of detecting positive pressures applied thereto. Examples of suitable pressure transducers include pressure sensors using strain gauges. Such pressure transducers may also contain protective films bonded directly on their inside surface to the strain gage. An example of this type of flush mount pressure transducer is the MP40 from Micron Instruments.

Referring to FIGS. 1 and 2, the blood pump 108 is a peristaltic pump that creates flow within a loop of tubing that is disposed in a circular pump raceway by rotating a frame that has several rollers attached to the frame. As the frame rotates, the rollers compress portions of the tubing and force small pockets of blood to flow within the loop of tubing.

The dialysis machine control unit 106 is electrically connected to and controls the operation of various mechanical and electrical systems of the dialysis system 100. The dialysis machine control unit 106 can control the operation of the blood pump 108, which circulates blood through the blood line set 104, and it can monitor pressure of the blood, as detected by the pressure transducers 160, 162, that flows through the blood line set 104. The dialysis machine control unit 106 can also control the operation of the dialysate pump(s) and heaters within the system to control the pressure, flow, and temperature of the dialysate within the dialysate fluid circuit.

Figure 3:
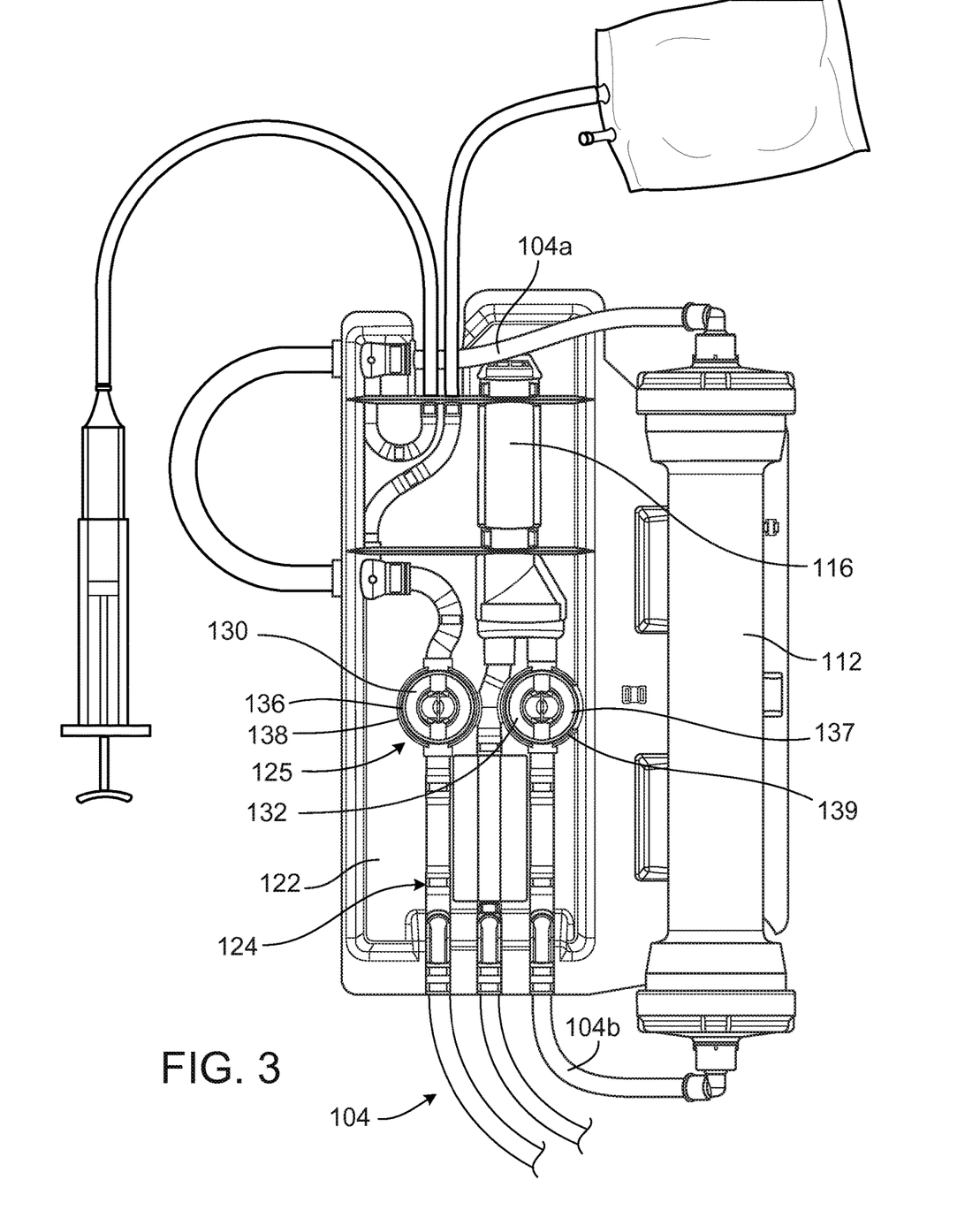
FIG. 3 is a schematic of the blood line set of FIG. 1.

Referring to FIG. 3, the disposable blood line set 104 includes a series of blood lines and components that are attached to a carrier 122. The carrier 122 includes a molded thermoplastic or thermoset body having hemispherical recesses 124 for capturing the blood lines and apertures 125 for capturing the various other components. In addition to holding the components in place, the apertures 125 allow for visual or instrument access to the components. The body of the carrier 122 can also include openings that receive pins extending from the face of the dialysis machine to hold the blood line set 104 in a desired position relative to the face of the dialysis machine 102.

The blood line segments upstream of the dialyzer 112 are referred to collectively herein as the arterial blood line 104a, while the blood line segments downstream of the dialyzer 112 are referred to collectively herein as the venous blood line 104b. Each of those lines is securely engaged within the hemispherical recesses 124 formed in the body of the carrier 122. The other components of the blood line set 104 include an air release chamber 116 and the arterial and venous pressure capsules 130, 132. These components are secured within the apertures 125, which both hold the components in place relative to the carrier 122 and permit sensors positioned on the face of the dialysis machine to engage or access the components.

Figure 4:
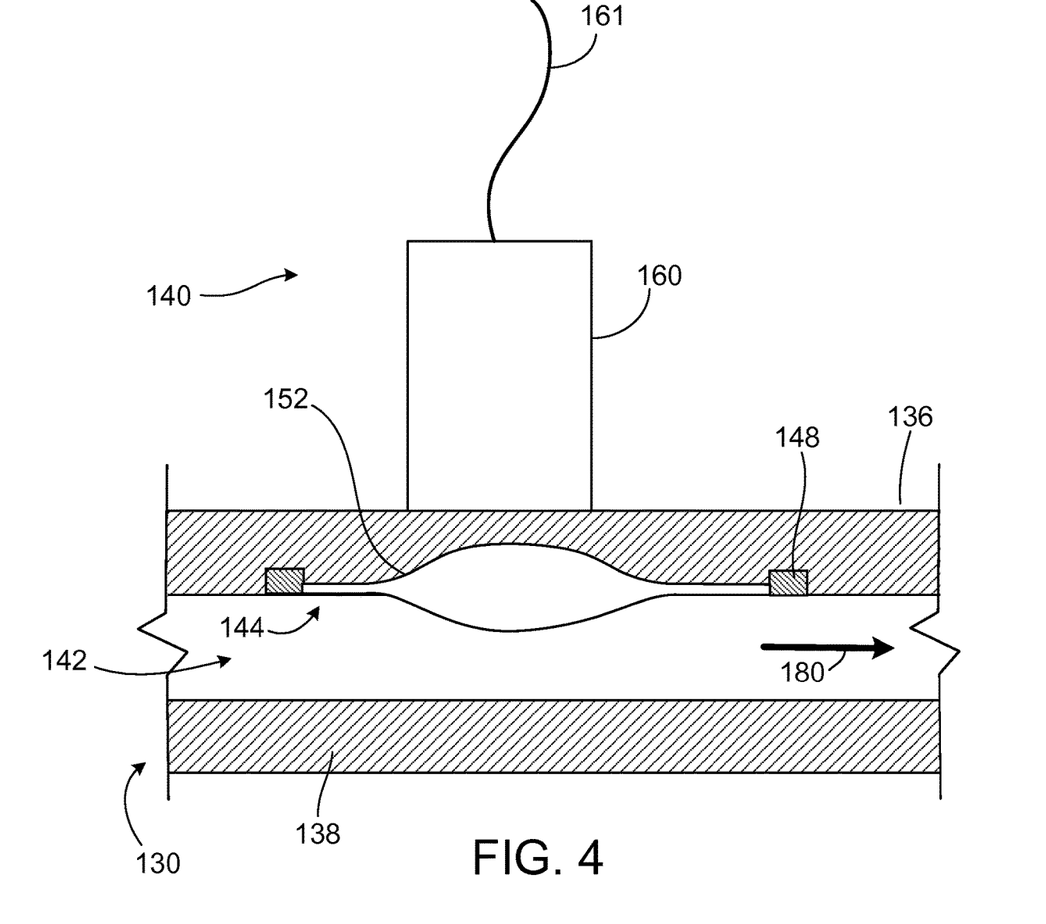
FIG. 4 is a cross-sectional view of a region of the blood line set of FIG. 1 secured to the hemodialysis machine, showing a diaphragm of a pressure capsule of the blood line set being pressed against a pressure transducer of the hemodialysis machine by an air pillow within the pressure capsule.

Still referring to FIG. 3, each of the pressure capsules 130, 132 includes a flexible diaphragm 136, 137 that is secured to a rigid cylindrical base 138, 139. The rigid base 138, 139 defines a channel that extends from a bottom region of the base to a top region of the base, and the diaphragm 136, 137 covers the channel to form a fluid passage 142 (shown in FIG. 4) between the base 138, 139 and the diaphragm 136, 137. The cylindrical base 138, 139 is the portion of the pressure capsule 130, 132 that is secured within the aperture 125 of the carrier 122. The diaphragm 136, 137 forms the surface of the pressure capsule 130, 132 that is pressed against the face of the dialysis machine 102 during treatment. When the blood line set 104 is secured to the dialysis machine 102, the pressure capsules 130, 132 align with the pressure transducers 160, 162 on the face of the dialysis machine 102 such that the diaphragms of the pressure capsules 130, 132 are pressed against the pressure transducers 160, 162. The pressure transducers 160, 162 together with the pressure capsules 130, 132 form pressure sensor assemblies 140, 141 that allow pressure to be sensed at different locations in the blood line set 104. FIG. 4 illustrates a cross-section of the pressure sensor assembly 140. The pressure sensor assembly 141 has an identical structure and function to the pressure sensor assembly 140 and will therefore not be separately described in detail. As shown in FIG. 4, the pressure capsule 130 includes an air pillow 152 formed between the diaphragm 136 and a membrane 144 that is attached to the diaphragm 136 by a perimeter seal 148. The membrane 144 can, for example, be thermally or adhesively bonded to the diaphragm 136. The air within the air pillow 152 is pressurized and, prior to the pressure capsule 130 being pressed against the face of the dialysis machine 102, causes the diaphragm 136 to protrude outwardly. It is this outwardly protruding portion of the diaphragm 136 that contacts and applies an initial positive pressure to the pressure transducer 160 when the pressure capsule 130 is secured to the face of the dialysis machine 102.

Still referring to FIG. 4, during treatment, the pressure transducer 160 cooperates with the pressure capsule 130 to measure the in-line blood pressure within the fluid passage 142 extending through the pressure capsule 130. The diaphragm 136 isolates the flush mount pressure transducer 160 from the blood within the pressure capsule 130. The air pillow 152 biases the diaphragm 136 of the pressure capsule 130 toward the pressure transducer 160. The diaphragm 136 and the air pillow 152 are deflected toward the pressure transducer 160 by positive fluid pressure in the fluid passage 142 of the pressure capsule 130. This deflection is sensed by the pressure transducer 160, which generates an electrical signal indicative of the positive fluid pressure on the diaphragm 136. A signal wire 161 transmits the sensor electrical signal to the control unit 106 which converts the signal into a corresponding blood pressure. Barometric pressure compensation can be applied by a barometric pressure sensor such as the Freescale MPL3115A2, or alternatively the sensor can be "zeroed" using an initial reading prior to treatment.

The pressure sensor assembly 140 is also configured to sense negative pressures generated in the fluid passage 142 extending through the pressure capsule 130. The fluid passage 142, as shown in FIG. 4, is bounded by the thin membrane 144 which cooperates with the diaphragm 136 of the pressure capsule 130 to form the air pillow 152. Fluid flowing through the fluid passage 142 along the direction of arrow 180 transmits force through both the thin membrane 144 and the diaphragm 136, which act as transmission elements between the fluid and the pressure transducer 160. The air pillow 152 acts as a displacement device 150 that creates a mechanical preload on the transducer 160. As described in greater detail below, this helps to ensure contact between the diaphragm 136 and the pressure transducer 160 as pressure variations in the fluid passage 142 cause the membrane 144 to expand and retract.

To maintain contact between the diaphragm 136 and the pressure transducer 160 even in the absence of positive fluid pressures within the fluid passage 142, the air pillow 152 of the pressure capsule 130 applies a pre-load to the pressure transducer 160. By creating a preload on the face of the transducer 160, a negative pressure within the pressure enclosure of fluid passage 142 will first act to relieve some of the preloaded pressure sensed by the transducer 160. As the preload pressure is unloaded from the transducer 160, the diaphragm 136 and the pressure transducer 160 maintain contact with one another so long as the negative pressure is less in magnitude than the positive pre-load pressure. Such a negative pressure is therefore measurable by the pressure transducer 160.

By creating a pillow 152 and compressing this pillow against the flush mount pressure transducer 160 a positive pressure offset in the system is created that can be accounted for during subsequent pressure measurements. In some cases, the pressure sensor assembly 140 can be used to measure +/−10 psi, while the flush mount pressure transducer 160 can measure up to 20 psi. By filling the air pillow 152 with an air pressure of 1 psi and compressing the air pillow 152 against the flush mount pressure transducer 160 with 10 psi of pressure, the resulting reading of the flush mount pressure transducer 160 will be 10 lbf (assuming 1 square inch of contact for simplicity) and the pressure in the pillow will be 11 psi (i.e., 10 psi+1 psi). Once the pressure transducer 160 and the air pillow 152 are compressed, the pressure transducer 160 is calibrated to read zero psi. If a negative pressure is then generated within the fluid passage 142 of the pressure capsule 130, which would tend to pull the membrane 144 away from the transducer 160, pressure on the air pillow 152 and thus the pressure transducer 160 will be first alleviated. This preload on the transducer 160 can allow for a negative pressure of up to the preloaded amount of 10 psi to be unloaded from the transducer 160 without losing contact between the diaphragm 136, and the pressure transducer 160, allowing the pressure sensor assembly 140 to read the negative pressure.

The pressure sensor assembly 140, as discussed above, also measures positive pressure within the fluid passage 142 of the pressure capsule 130. Positive pressure is additive as well and will create an additional positive pressure on the flush mounted pressure transducer 160. The maximum negative and positive pressure readings are limited by the sensor range of the particular transducer and by the initial offset pressure. In the example above, the 20 psi range of the transducer calibrated to read 0 psi with 10 psi preloaded onto the transducers allows blood pressures to be measured from −10 psi to +10 psi relative to the zero calibration.

Because this initial zero point of the transducer 160 is calibrated, the pressure inside the offset pillow 152 itself does not affect the translated pressure from the blood onto the flush mounted transducer 160. This allows a wide variation in the pressure of offset pillow 152. The offset pillow 152, membrane 144 and diaphragm 136 move in synchronism independent of the fluid pressure. Thus, positive as well as negative pressures can be transmitted from the membrane 144 to the diaphragm 136, without the costly vacuum sealing currently used in some systems to maintain the transmissive films against a transducer face.

Referring again to FIGS. 1 and 3, during a hemodialysis treatment, blood is removed from a patient and circulated through the blood line set 104 to remove waste from the blood. On the arterial side of the extracorporeal fluid circuit, blood is drawn from the patient through the arterial tubing 104a of the blood line set 104 to the dialyzer 112. The pressure sensor assembly 140 monitors the blood pressure in the pressure capsule 130 upstream of the blood pump 108. Because the pressure sensor assembly 140 is located upstream of the blood pump 108, negative pressures will typically be generated in the pressure capsule 130 of the pressure sensor assembly 140. Using the air pillow 152 to apply a pre-load pressure to the pressure transducer 160 in the manner described above helps to ensure that these negative pressures can be reliably detected by the pressure transducer 160. The pressure detected by the pressure sensor assembly 140 can be used to control the blood pump 108. For example, upon measuring a pressure that lies outside an acceptable pressure range, the control unit 106 of the dialysis machine 102 can activate an alarm and automatically stop the blood pump 108.

Assuming no such alarm occurs, the blood pump 108 continues to run and forces the blood through the arterial tubing 104a to the dialyzer 112. As the blood flows through a first chamber of the dialyzer 112 in one direction, dialysate is pumped through a second chamber of the dialyzer 112 in an opposite direction. During this process, toxins pass from the blood to the dialysate through a semi-permeable surface (e.g., semi-permeable micro tubes) that separate the first and second chambers of the dialyzer 112. As a result, the blood is filtered.

The filtered blood then is pumped through the venous tubing 104b of the blood line set 104. The blood flows from the dialyzer 112, passing through the pressure capsule 132, the air release chamber 116, and various sensors, before returning to the patient 120 via the venous tubing 104b. The air release chamber 116 includes both an entry port and an exit port. In some implementations, the pressure sensor region 132 leads directly into entry port of the air release chamber 116 with no tubing therebetween. In other implementations, a short piece of tubing connects capsule 134 with air release chamber 116.

The pressure sensor assembly 141 monitors the blood pressure within the pressure capsule 132. Because the pressure sensor assembly 141 is located downstream from the blood pump 108, the pressures within the pressure capsule 132 will typically be positive. These pressure measurements can be used to control the blood pump 108. For example, upon measuring a pressure that lies outside an acceptable pressure range, the control unit 106 of the dialysis machine 102 can activate an alarm and automatically stop the blood pump 108.

While the pressure capsule 130 has been described as including an air pillow to apply the pre-load force to the pressure transducer 160, other types of fluid pillows can alternatively be used. In some implementations, for example, a liquid pillow is used to apply the pre-load force to the pressure transducer.

Figure 5:
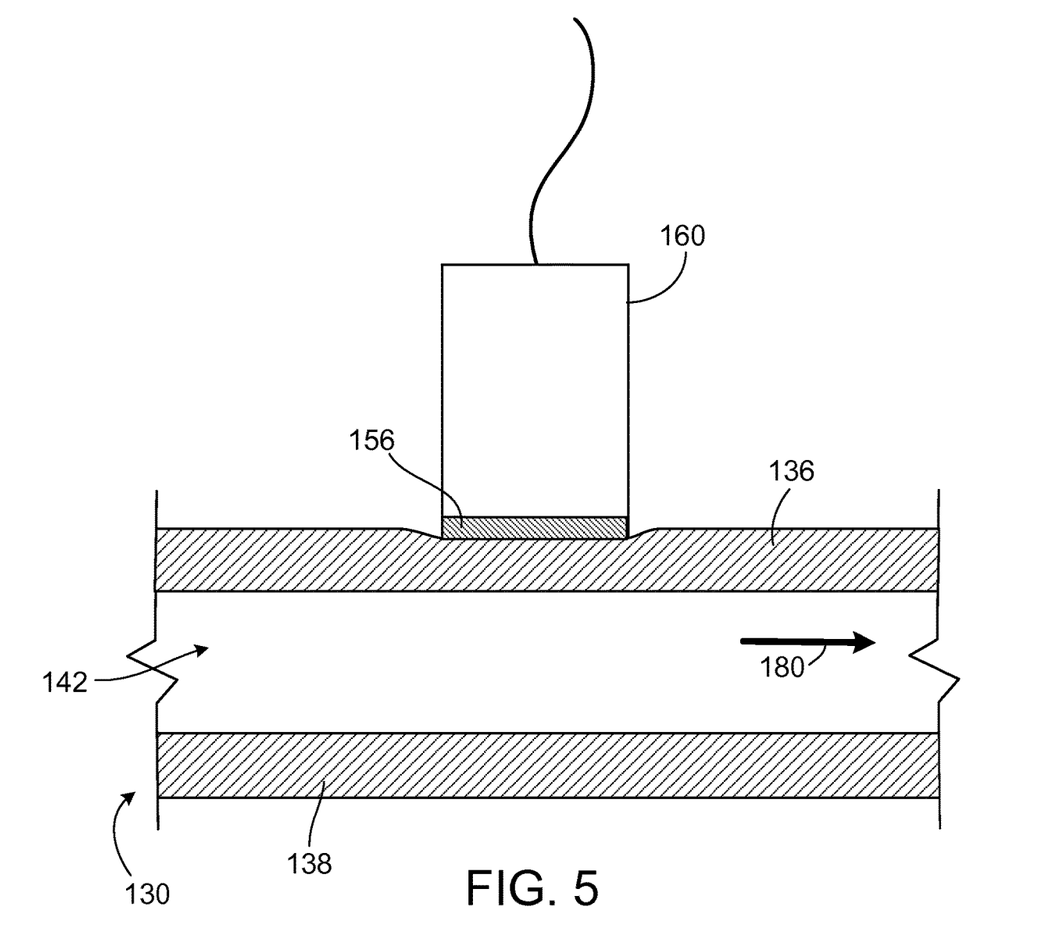
FIG. 5 is a cross-sectional view of a region of another blood line set secured to the hemodialysis machine of FIG. 1, showing a diaphragm of a pressure capsule of the blood line set being pressed against the pressure transducer of the hemodialysis machine by a disc affixed to the diaphragm.

In further implementations, alternate devices are used to mechanically create a preload on the pressure transducer 160. FIG. 5 shows an implementation in which an offset disc 156 replaces the offset pillow 152. The offset disc 156 is a solid plastic disc that is affixed to the outside of diaphragm 136. The offset disc 156 is relatively inflexible compared to the diaphragm 136 and stretches the diaphragm 136 as the pressure capsule 130 is pressed against the pressure transducer 160. This stretch results in an increased force on the transducer 160, resulting in the preload force being felt by the transducer even when the fluid passage 142 within the pressure capsule 130 is at atmospheric pressure. Similarly as described for the offset pillow 150, the transducer 160 can be calibrated to measure zero pressure when the nonzero pressure resulting from the disc 156 is pressed against it.

While the disc 156 has been described as being affixed to the outside of diaphragm 136, the disk can alternatively be affixed to the inside of diaphragm 136, in the location shown for offset pillow 152. Alternatively, the disc may be integrated into diaphragm 136, and be of sufficient size and stiffness to generate the desired offset pressure against transducer 160.

While the disc 156 has been described as being formed of plastic, the disk can alternatively be formed of one or more other materials that are relatively incompressible, including metals and alloys.

Figure 6:
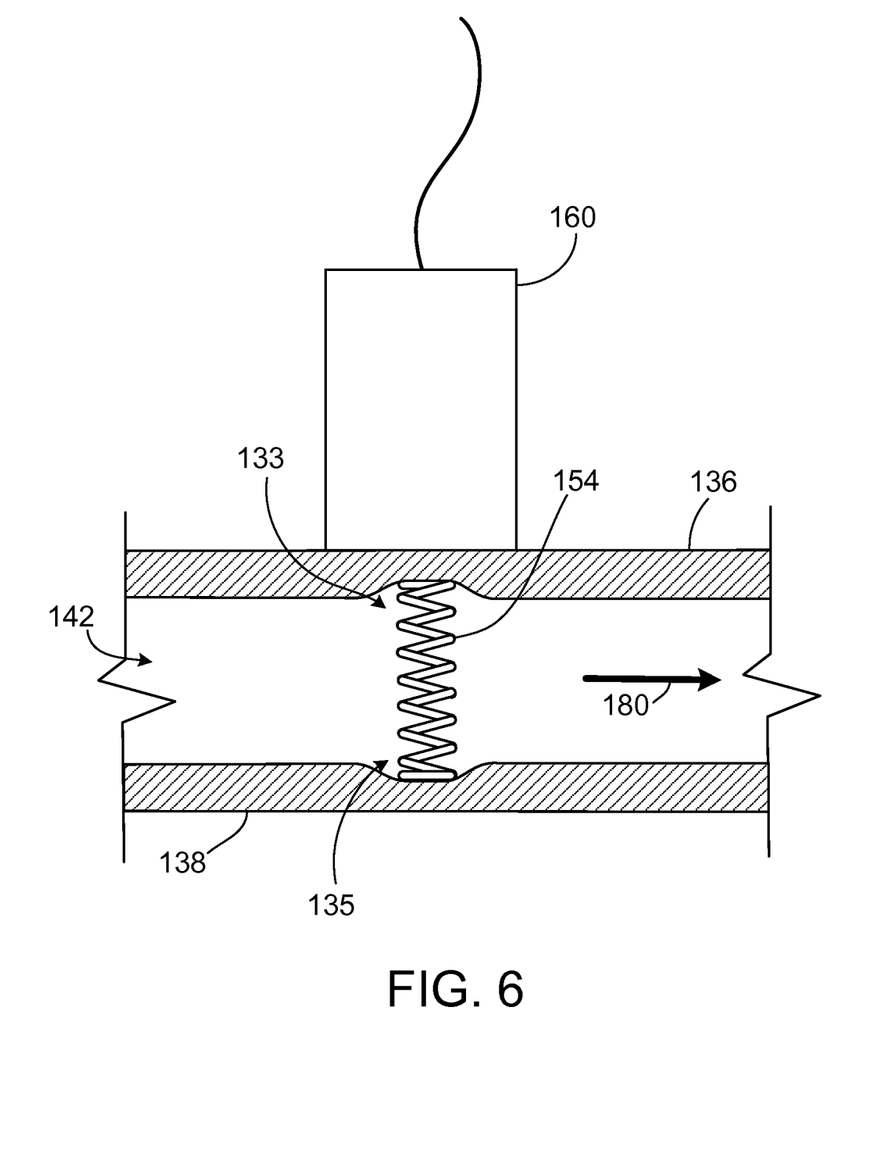
FIG. 6 is a cross sectional view of a region of a different blood line set secured to the hemodialysis machine of FIG. 1, showing a diaphragm of a pressure capsule of the blood line set being pressed against the pressure transducer of the hemodialysis machine by a spring disposed within a fluid passage of the pressure capsule.

FIG. 6 shows an alternative implementation in which a spring 154 is placed in the blood flow of the fluid passage 142 of the pressure capsule 130. The dimensions and elasticity of the spring 154 can be chosen to place a known pressure on the pressure transducer 160 when the blood line set is secured to the dialysis machine 102. Diaphragm 136 may contain a seat 133 and base 138 may similarly contain a divot 135 into which the spring 154 is affixed. Similarly as described for the offset air pillow 152 above, the transducer 160 can be calibrated to measure zero pressure when the nonzero pressure resulting from the spring 154 is pressed against it. The spring 154 can be made of plastic or other material suitable for being immersed in the blood flowing through fluid passage 142.

While the spring 154 has been described as being disposed within the fluid passage 142, in some implementations, a spring is attached to an outer surface of the diaphragm 136 and is configured to make direct contact with the pressure transducer 160 when the blood line set is secured to the face of the dialysis machine 102. The resistance of the diaphragm 136 to stretching in combination with the spring force of the spring results in a pre-load being applied to the pressure transducer 160 when the blood line set is secured to the machine.

Figure 7:
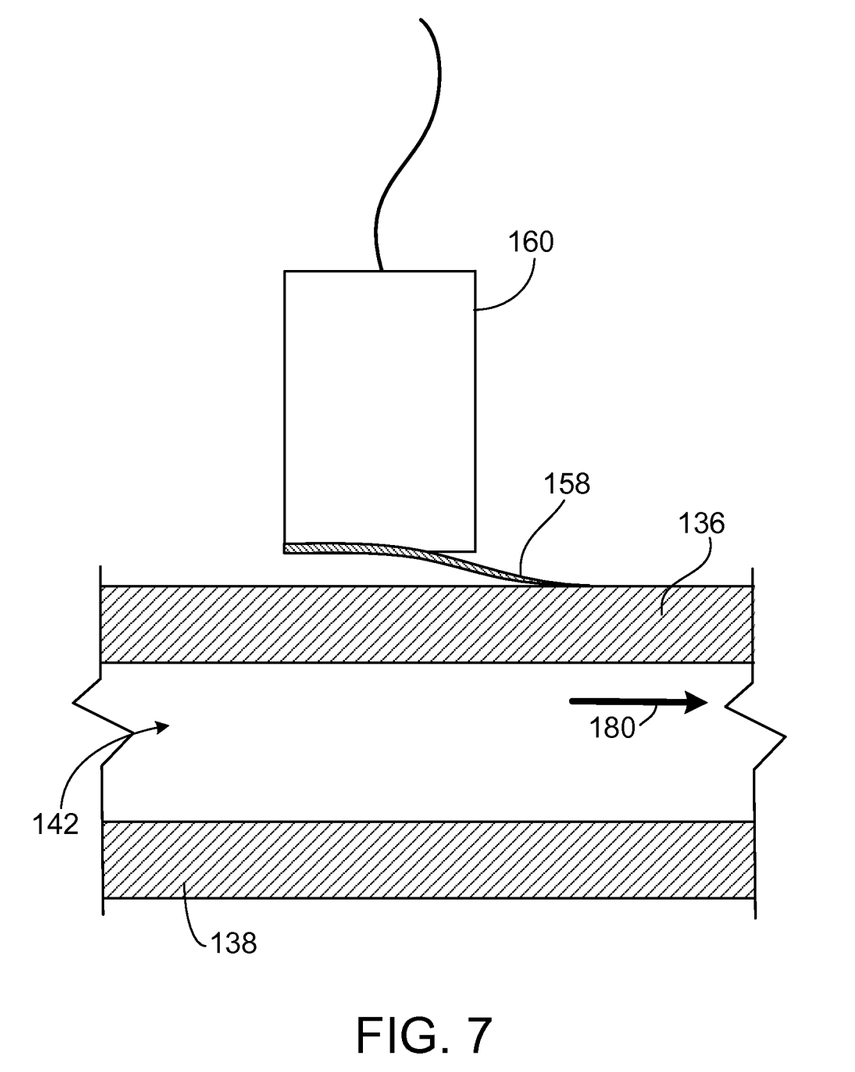
FIG. 7 is a cross-sectional view of a region of another blood line set secured to the hemodialysis machine of FIG. 1, showing a diaphragm of a pressure capsule of the blood line set being pressed against the pressure transducer of the hemodialysis machine by a leaf spring acting on the diaphragm.

FIG. 7 shows an alternative implementation in which a spring (e.g., a leaf spring) 158 is attached to the outer surface of the diaphragm 136. When the pressure capsule is attached to the face of the dialysis machine 102, the leaf spring 158 contacts the pressure transducer 160 resulting in the desired mechanical preload on the transducer. Similarly as described for the offset pillow 152 above, the transducer 160 can be calibrated to measure zero pressure when the nonzero pressure resulting from the lever arm or leaf spring 158 is pressed against it.

While the leaf spring 158 has been described as being attached to the outer surface of the diaphragm 136, the leaf spring 158 can alternatively be attached to the inner surface of the diaphragm 136 in which case the force of the leaf spring 158 would press the diaphragm 136 against the pressure transducer 160 to provide the pre-load pressure to the pressure transducer 160.

In the implementations described above the sensor 140 uses a mechanical force rather than a vacuum or pneumatic connection to ensure contact between the respective pressure transmission elements and to enable negative pressure readings. Other mechanical loading devices are also envisioned, and are integratable into the pressure sensor assembly.

In the implementations described, there may be some pressure measurement distortion due to compliance or non-linearity of the offset devices (i.e., the air pillow, springs, etc.) which can be measured and corrected. For example, the offset pillow 152 of FIG. 4, the stretched diaphragm 136 of FIG. 5, the spring 154 of FIG. 6, and the leaf spring 158 of FIG. 7 may cause nonlinearities in compliance. Pressure in the fluid passage 142 of the pressure capsule 130 is measurable by using a corrective device, such as a look-up table or nonlinear algorithm that can recover the actual pressure reading. To do so, the dialysis machine control unit 106 accesses a look-up table 170 that contains corrected fluid pressures based on the fluid pressure measurement for the specific type of pressure sensor assembly being used.

Such a look-up table 170 is populated with corrected blood pressure readings for each of the measured positive or negative pressure readings measured by the pressure sensor assembly. The appropriate corrected fluid pressure reading is then used by the dialysis system 100 to help ensure that the fluid circulated through the blood line set 104 is maintained within a desired pressure. In order to populate the look-up table with corrected blood pressures, a series of experiments is performed to empirically determine the correlation between actual fluid pressure in the fluid passage 142 and the pressure measured by pressure sensor assembly for a given type of offset device. Corrected pressures are determined simulating treatment under various conditions for the full range of pressures desired. The populated look-up table is loaded into the dialysis machine control unit 106. The control unit 106 is configured such that during treatment the control unit 106 can access the table, and the dialysis system 100 can determine a more accurate fluid pressure measurement to be used by the system.

If the pressure measurements are not on the look-up table, the control unit 106 of the dialysis machine 102 can implement linear interpolation or similar numerical methods to estimate a corrected blood pressure based on the closest pressure intervals provided in the look-up table. The control unit can alternatively or additionally include a system of equations to calculate a corrected fluid pressure based on a given fluid pressure measured by the pressure transducer. For example, the relationship between the two pressures could be exponential, and the control unit 106 would take the logarithm of the measured pressure to calculate the actual pressure. Alternatively, instead of using the test data discussed above to populate a table of corrected pressures, the test data can be manipulated using common numerical method techniques to obtain a system of equations correlating the measured and actual fluid pressures. As the type of tubing used affects the pressure measurements, there would be particular equations for particular tubing types as well as particular displacement or offset devices.

Although the pressure sensor assemblies are described as being calibrated to read zero with the displacement devices adding a preload to the pressure transducer 160 and absent any liquid (e.g., blood) in the system, this is not necessary for subsequent accurate readings using the pressure sensor assembly 140. Calibration of the transducer 160 to zero when preloaded by a displacement device permits subsequent pressure measurements to be directly read as positive or negative relative to the offset pressure value. However, if this re-zeroing calibration is not carried out, the pressure transducer 160 will measure "positive" pressures +/− the offset pressure. The look-up table or numerical methods described above can be modified to take the offset pressure into account.

While the pressure capsule 132, which is used to measure the pressure of blood after the blood exits the dialyzer 112, has been described as being positioned upstream of the air release chamber 116, the pressure capsule 132 can alternatively be positioned along the venous tubing 104b after the air release chamber 116.

While the carrier 122 of the blood line set 104 has been described as including openings that receive pins extending from the face of the dialysis machine 102 to hold the blood line set 104 in a desired position relative to the face of the dialysis machine 102, any of various other techniques can alternatively or additionally be used for this purpose. The dialysis machine can, for example, include clips, clamps, magnets, etc., for securing the blood line set in a desired position relative to the face of the dialysis machine.

The pressure sensor assemblies 140, 141 have been described as measuring the pressure of blood being removed from and returned to the patient. Similar pressure sensor assemblies can be used to measure the pressure of dialysate circulating within the dialysate fluid circuit.

While the hemodialysis systems discussed above have been described as including disposable line sets having a series of lines (i.e., blood lines and/or dialysate lines) connected to a carrier member and having pressure capsules positioned along the lines, the systems can alternatively or additionally include medical fluid cassettes (e.g., blood cassettes and/or dialysate cassettes) having integrated fluid lines and pressure capsules. Such a cassette typically includes a rigid base to which a diaphragm is secured. The rigid base includes recesses, and the diaphragm cooperates with those recessed portions of the rigid base to form fluid passages and pressure capsules.

Although each of the pressure sensor assemblies discussed above has been described as being part of a hemodialysis system, the pressure sensor assemblies could also be used in the place of current pressure sensors in peritoneal dialysis systems. The pressure sensor assemblies described herein could, for example, be used to replace either passive vacuum sensors or active vacuum sensors currently used in such machines. The pressure sensor assemblies can be used in peritoneal dialysis systems to determine corrected pressure values of dialysate flowing to and/or from a patient. In such implementations, the pressure sensor assemblies are connected to a dialysate line in much the same way as they are described above as being connected to the blood lines.

Figure 8:
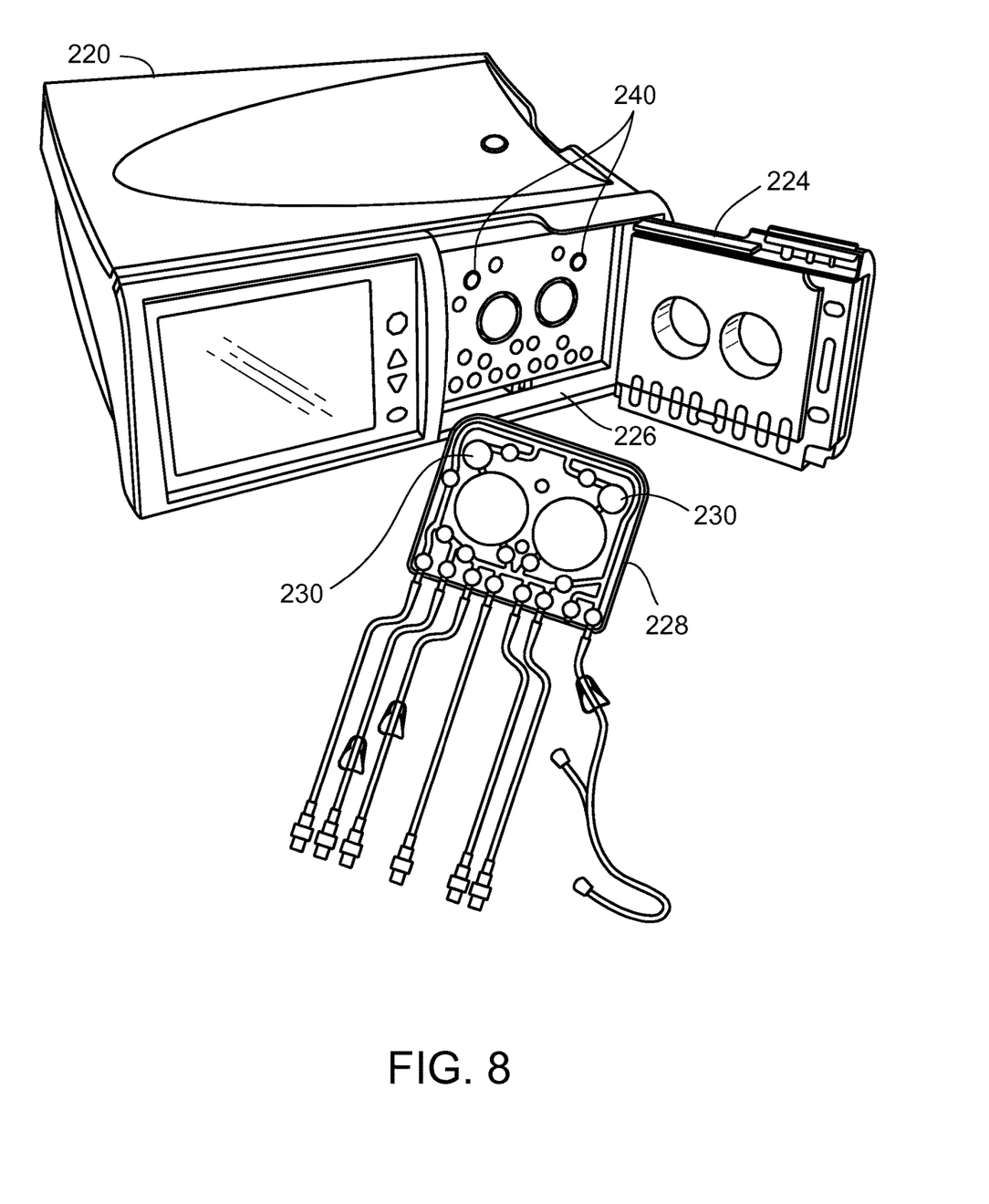
FIG. 8 is a schematic of a peritoneal dialysis system including a peritoneal machine having a pressure transducer and a peritoneal dialysis fluid cassette having a pressure capsule that aligns with and applies a pre-load pressure to the pressure transducer.

FIG. 8 illustrates a peritoneal dialysis system that utilizes pressure sensor assemblies of the type described above. The peritoneal dialysis system includes a peritoneal dialysis machine 220 and a dialysate cassette 228. The peritoneal dialysis machine 220 includes a hinged door 224 and a cassette support area 226. The cassette 228 fits into the cassette support area 226 and the door 224 is closed upon the cassette and securely latched.

When the cassette 228 is loaded into the peritoneal dialysis machine between the door 224 and the cassette support area 226, integrated pressure capsules 230 of the cassette 228 align with and contact corresponding pressure sensors 240 that are flush-mounted in the cassette support area 226. The pressure capsules 230 and the pressure sensors 240 can be configured in the same way as any of the various pressure capsules and pressure transducers described above to form pressure sensor assemblies that permit both positive and negative fluid pressures within the pressure capsules 230 to be detected by the pressure sensors 240. The pressure capsules 230 are fluidly connected to the patient so that when fluid moves through the cassette 228, the pressure sensors 240 can detect the pressure.

While the displacement device or offset device (i.e., the air pillow, disc, spring, etc.) is part of the pressure capsule in each of the implementations discussed above, the displacement device or offset device can alternatively be part of the pressure transducer 160. For example, an air pillow, disc, or spring can be attached to the face of the pressure transducer 160 to provide a pre-load pressure to the presser transducer when a pressure capsule that includes no such displacement or offset device is connected to the dialysis machine. In certain cases, a thick film is attached to a face of the pressure transducer and performs a similar function to the offset devices discussed above. Alternatively, the pressure transducer can otherwise be extended outwardly from the face of the machine to ensure that, when the disposable line set is secured to the machine, a pre-load force is applied to the pressure transducer.

While the pressure sensor assemblies discussed above have been described as being used in dialysis systems, the pressure sensor assemblies can be used in other types of blood treatment and processing systems, such as cardio pulmonary by-pass systems, blood transfusion systems, apheresis systems, and plasmapheresis systems. For example, ultrafiltration machines for the treatment of patients suffering from heart failure, acute or chronic renal failure or body fluid excess can use the pressure sensor assemblies to measure the pressure of blood being withdrawn from and returned to the patient.

Other implementations are within the scope of the following claims.

What is claimed is:

1. A medical system comprising:
    a medical fluid pumping machine comprising a pressure sensor flush mounted on a face of the medical fluid pumping machine;
    a medical fluid line set comprising a fluid line in fluid communication with a fluid passage formed between a flexible diaphragm and a base, the medical fluid line set being configured to be connected to the medical fluid pumping machine in a manner such that the flexible diaphragm of the medical fluid line set aligns with and contacts a face of the flush mounted pressure sensor of the medical fluid pumping machine; and
    a fluid pillow formed between the flexible diaphragm and a membrane that is attached to the flexible diaphragm, the fluid pillow being configured to a) cause the flexible diaphragm to protrude outwardly prior to the medical fluid line set being connected to the medical fluid pumping machine and b) apply a positive force to the flush mounted pressure sensor when the medical fluid line set is connected to the medical fluid pumping machine and the fluid passage is at atmospheric pressure.

2. The medical system of claim 1, wherein the flexible diaphragm and the base are parts of a pressure capsule to which the fluid line is connected.

3. The medical system of claim 1, wherein the flexible diaphragm and the base are parts of a medical fluid cassette to which the fluid line is connected.

4. The medical system of claim 1, wherein the fluid pillow enables the pressure sensor to detect positive and negative pressures generated within the fluid passage.

5. The medical system of claim 1, wherein the fluid pillow is an air pillow.

6. The medical system of claim 5, wherein the air within the air pillow is pressurized.

7. The medical system of claim 1, wherein the fluid pillow is configured to press the flexible diaphragm against the pressure sensor to apply the positive force to the pressure sensor when the medical fluid line set is connected to the medical fluid pumping machine.

8. The medical system of claim 1, wherein the pressure sensor is configured to contact an outer surface of the flexible diaphragm when the medical fluid line set is connected to the medical fluid pumping machine.

9. The medical system of claim 1, wherein the pressure sensor is configured to be calibrated to a zero reading while the positive force is applied to the pressure sensor.

10. The medical system of claim 1, further comprising a control unit that is in communication with the pressure sensor and is configured to determine a medical fluid pressure based on a pressure detected by the pressure sensor.

11. The medical system of claim 10, wherein the control unit comprises a look-up table that provides a corrected fluid pressure for each pressure detected by the pressure sensor.

12. The medical system of claim 10, wherein the control unit is configured to calculate a corrected medical fluid pressure by inputting a pressure detected by the pressure sensor into an equation.

13. The medical system of claim 1, wherein the pressure sensor comprises a pressure transducer.

14. The medical system of claim 1, wherein the medical fluid pumping machine is a dialysis machine.

15. The medical system of claim 1, wherein the medical fluid pumping machine is a blood pumping machine and the pressure sensor is configured to detect a pressure of blood within the fluid passage.

16. The medical system of claim 1, wherein the membrane is attached to the flexible diaphragm by a perimeter seal.

17. The medical system of claim 1, wherein the fluid pillow is configured to hold the flexible diaphragm in contact with the pressure sensor during both negative pressure measurement and positive pressure measurement.

18. A medical fluid line set comprising:
a fluid line in fluid communication with a fluid passage formed between a flexible diaphragm and a base, the medical fluid line set being configured to be connected to a medical fluid pumping machine in a manner such that the flexible diaphragm of the medical fluid line set aligns with and contacts a face of a pressure sensor flush mounted on a face of the medical fluid pumping machine; and
a fluid pillow formed between the flexible diaphragm and a membrane that is attached to the flexible diaphragm, the fluid pillow being configured to a) cause the flexible diaphragm to protrude outwardly prior to the medical fluid line set being connected to the medical fluid pumping machine and b) apply a positive force to the pressure sensor when the medical fluid line set is connected to the medical fluid pumping machine and the fluid passage is at atmospheric pressure.

19. The medical fluid line set of claim 18, wherein the flexible diaphragm, the base, and the fluid pillow are parts of a pressure capsule to which the fluid line is connected.

20. The medical fluid line set of claim 18, wherein the flexible diaphragm, the base, and the fluid pillow are parts of a medical fluid cassette to which the fluid line is connected.

21. The medical fluid line set of claim 18, wherein the fluid pillow is an air pillow.

22. The medical fluid line set of claim 21, wherein the air within the air pillow is pressurized.

23. The medical fluid line set of claim 18, wherein the fluid pillow is configured to hold the flexible diaphragm in contact with the pressure sensor during both negative pressure measurement and positive pressure measurement.

24. A medical fluid pumping machine comprising:
a pressure sensor flush mounted on a face of the medical fluid pumping machine, wherein the pressure sensor is arranged to align with and contact a flexible diaphragm of a medical fluid line set when the medical fluid line set is connected to the medical fluid pumping machine, wherein the flexible diaphragm of the medical fluid line set overlies a fluid pillow formed between the flexible diaphragm and a membrane that is attached to the flexible diaphragm, the fluid pillow being that configured to cause the flexible diaphragm of the fluid line set to (i) protrude outwardly prior to the medical fluid line set being connected to the medical fluid pumping machine and (ii) apply a positive force to the flush mounted pressure sensor when the fluid line set is connected the medical fluid pumping machine.

25. The medical fluid pumping machine of claim 24, wherein the pressure sensor is configured to be calibrated to a zero reading while a positive force is applied to the pressure sensor by the medical fluid line set.

26. The medical fluid pumping machine of claim 24, further comprising a control unit that is in communication with the pressure sensor and is configured to determine a medical fluid pressure based on a pressure detected by the pressure sensor.

27. The medical fluid pumping machine of claim 24, wherein the pressure sensor comprises a pressure transducer.

* * * * *

UNITED STATES PATENT AND TRADEMARK OFFICE
CERTIFICATE OF CORRECTION

PATENT NO.         : 10,912,875 B2
APPLICATION NO.    : 14/510199
DATED              : February 9, 2021
INVENTOR(S)        : Michael James Beiriger It is certified that error appears in the above-identified patent and that said Letters Patent is hereby corrected as shown below:

In the Claims

Column 14, Line 32, In Claim 24, after "being" delete "that".

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*